US010968154B2

(12) United States Patent
DeGreeff et al.

(10) Patent No.: US 10,968,154 B2
(45) Date of Patent: Apr. 6, 2021

(54) DERIVITIZATION OF VAPOROUS CHLORINE BY PROPYLENE OXIDE

(71) Applicant: The Government of the United States of America, as represented by the Secretary of the Navy, Arlington, VA (US)

(72) Inventors: Lauryn E. DeGreeff, Washington, DC (US); Janet M. Crespo Cajigas, San Juan, PR (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 16/778,208

(22) Filed: Jan. 31, 2020

(65) Prior Publication Data
US 2020/0247736 A1     Aug. 6, 2020

Related U.S. Application Data (60) Provisional application No. 62/799,875, filed on Feb. 1, 2019.

(51) Int. Cl.
| | | |
|---|---|---|
| *C07C 29/62* | (2006.01) | |
| *G01N 1/30* | (2006.01) | |
| *G01N 30/02* | (2006.01) | |
| *G01N 30/06* | (2006.01) | |

(52) U.S. Cl.
CPC ............... *C07C 29/62* (2013.01); *G01N 1/30* (2013.01); *G01N 30/02* (2013.01); *G01N 2030/025* (2013.01); *G01N 2030/067* (2013.01)

(58) Field of Classification Search
CPC .. C07C 29/62; G01N 30/02; G01N 2030/025; G01N 2030/067; G01N 1/30; G01N 31/22
See application file for complete search history.

(56) References Cited

U.S. PATENT DOCUMENTS

| 4,283,577 A * | 8/1981 | Jequier ................ C07C 29/64 |
| | | 568/614 |
| 9,733,234 B2 * | 8/2017 | Pawliszyn .............. G01N 1/405 |
| 2014/0021270 A1 * | 1/2014 | MacCrehan ........... B65D 77/00 |
| | | 239/10 |
| 2018/0246070 A1 * | 8/2018 | DeGreeff ............... G01N 30/30 |

FOREIGN PATENT DOCUMENTS

| JP | 58146521 A * | 9/1983 | ............. C07C 27/00 |

OTHER PUBLICATIONS

Jedrkiewicz et al. ("Application of modern sample preparation techniques to the determination of chloropropanols in food samples", Trends in Analytical Chemistry, vol. 62, 2014, pp. 173-183).*
Stewart et al. ("Reaction of Propylene Oxide with Hydrogen Halides", Contributions from the Department of Chemistry of the University of Kansas, ACS, vol. 76, Mar. 1954, pp. 1259-1264).*
Segura et al. ("Derivatization procedures for gas chromatographic-mass spectrometric determination of xenobiotics in biological samples, with special attention to drugs of abuse and doping agents", Journal of Chromatography B, 713, 1998, pp. 61-90).*
Cajigas et al., "Headspace analysis of potassium chlorate using on-fiber SPME derivatization coupled with GC/MS" Talanta 205 (2019) 120127, 1-6.
Esposito et al., "Determination of Ethylene Oxide in Air by Gas Chromatography" Anal. Cham. 1984, 56, 1950-1953.
Fiorenza et al., "Regiospecific Conversion of Oxiranes into Primary Alcohols via Reaction with Organotin Derivatives" Synthesis 1983, 640-641.
Tsai et al., "D etermination of ethylene oxide by solid-phase microextraction device with on-fiber derivatization" Journal of Chromatography A, 991 (2003) 1-11.

* cited by examiner

*Primary Examiner* — Rosalynd A Keys
(74) *Attorney, Agent, or Firm* — US Naval Research Laboratory; Joseph T. Grunkemeyer (57) ABSTRACT

Disclosed is a method of: providing a fiber having propylene oxide adsorbed thereon; exposing the fiber to a gaseous sample; allowing the propylene oxide to react with any chlorine in the sample to form chloro-2-propanol. The method can be used to detect potassium chlorate.

12 Claims, 8 Drawing Sheets

DERIVITIZATION OF VAPOROUS CHLORINE BY PROPYLENE OXIDE

This application claims the benefit of U.S. Provisional Application No. 62/799,875, filed on Feb. 2, 2019. The provisional application and all other publications and patent documents referred to throughout this nonprovisional application are incorporated herein by reference.

TECHNICAL FIELD

The present disclosure is generally related to detection of chlorine.

DESCRIPTION OF RELATED ART

Chlorine ($Cl_2$) is a diatomic gas in the halogen family. It is used in manufacturing, chemical synthesis, as well as in common household and industrial cleaning processes. It has also been used at high concentration as a chemical weapon. It is described to have a suffocating, bleach-like odor. Even at low levels (ppm-range) chlorine gas is toxic by inhalation and at even lower levels long-term exposure can cause respiratory damage (National Center for Biotechnology Information, "PubChem Compound Database—Chlorine (CID=24526)" National Institute for Health, [Online] Available: https://pubchem.ncbi.nlm.nih.gov/compound/24526 [Accessed 10 Aug. 2018]). The National Institute for Occupational Safety and Health (NIOSH) places occupational safety limits of chlorine in the air at 0.5 ppm (1.45 mg/m$^3$) (National Institute for Occupational Safety and Health, "NIOSH Pocket Guide to Chemical Hazards—Chlorine" Center for Disease Control and Prevention, 11 Apr. 2016. [Online] Available: https://www.cdc.gov/niosh/npg/npgd0115.html [Accessed 10 Aug. 2018]).

There is a variety of commercially available instrumentation or sensors and published methods for chlorine gas detection. This includes colorimetry (California Air Resources Board, "Method 434—Determination of chlorine in unheated air" State of California (1990)), electrochemical detection (Mil-Ram Technology, "Model TA-2100 Smarter Chlorine CL2 Gas Detector" [Online] Available: http://www.mil-ram.com/gas-detectors/data-sheets/chlorine-detector-ta2100.pdf [Accessed 10 Aug. 2018]; Occupational Safety and Health Administration, "OSHA Method ID 101—Chlorine in workplace atmospheres" American Conference of Governmental Industrial Hygienists, Cincinnati, Ohio (1991)), photoionization detection, infrared spectroscopy (Avenell, "Upgrading from Pellistor Gas Sensors to infrared technology" Crowcon Detection Instruments, February 2010. [Online] Available: http://halmapr.com/news/crowcon/2010/02/02/upgrading-from-pellistor-gas-sensors-to-infrared-technology/. [Accessed 10 May 2018]; Asimellis et al., "Controlled inert gas environment for enhanced chlorine and fluorine detection in the visible and near-infrared by laser-induced breakdown spectroscopy" *Spectrochimica Acta Part B: Atomic Spectroscopy*, 60(7-8), 1132-1139 (2005)), and laser-induced breakdown spectrometry (LIBS) (Cramers et al., "Detection of chlorine and fluorine in air by laser-induced breakdown spectrometry" *Analytical Chemistry*, 55, 1252-1256 (1983)). The performance of these techniques differ having detection limits ranging from 0.1 ppm to 8 ppm, but none of the techniques allow for pre-concentration of analyte vapor which improves detection of trace vapors or separation for avoidance of interferents from high background environments.

For occupational hazard monitoring, analyte concentrations may be very low, thus methods utilizing pre-concentration have been developed. NIOSH published a method for detection of chlorine in operational settings in 1994 using a personal sampling pump containing a silver-membrane filter for pre-concentration of air flowing at 0.3-1 L/min. Chlorine collected on the filter is then removed by dissolution in water, and the solution is analyzed using ion chromatography (National Institute of Occupational Safety and Health, "Chlorine—Method 6011," in *NIOSH Manual of Analytical Methods*, 4th ed., Center for Disease Control and Prevention (1994)). Additional methods for personal monitoring of chlorine were published by the State of California in 1990 (California Air Resources Board, "Method 434—Determination of chlorine in unheated air" State of California (1990)) and OSHA in 1991 (Occupational Safety and Health Administration, "OSHA Method ID 101—Chlorine in workplace atmospheres" American Conference of Governmental Industrial Hygienists, Cincinnati, Ohio (1991)). The California method requires suspect air to be bubbled through an acidified methyl orange solution resulting in a color change should chlorine be present in the air stream. The OSHA method also requires a bubbler containing 0.1% sulfamic acid solution. The resulting solution is then added to a potassium iodide buffer and chlorine is measured by a residual chlorine ion-specific electrode. All of these methods suffer from complex and labor-intensive protocols that are prone to false positives and sensitive to interferences, though the NIOSH method uses ion chromatography, a separation technique that reduces issues with interferences and false alarms to some degree.

Over the last two decades the availability of military and commercial explosives for illicit purposes has increased. At the same time, access to the internet has given potential hobbyists and terrorists an endless amount of information on formulation and synthesis of homemade explosives (HMEs). Finally, many HMEs are relatively simple mixtures of oxidizer and fuel, many of which can be derived from commercial products. These factors have led to an increased number of HME-related incidents over this period (Simon et al., "Canine detection of explosives: Shifting focus from traditional to homemade explosives (NRL/MR/6181--18-9794)" Naval Research Laboratory, Washington, D.C. (17 Sep. 2018)). Unfortunately, there has not been a proportionate increase in fundamental research on such materials, hindering development of new approaches for detection of HMEs. As a result, detection methods for HMEs are still not as numerous or robust as those found for traditional explosives, such as TNT (DeGreeff et al., "Considerations in the vapor analysis of traditional vs. homemade explosives" in *ISOCS/IEEE International Symposium on Olfaction and Electronic Nose*, Montreal, QC, Canada (2017)).

Potassium chlorate is a powerful oxidizer commercially available in pyrotechnics and certain household products. Currently, there are no known methods of vapor detection for potassium chlorate, outside of canine detection. Detection is challenging as it is an inorganic salt with no appreciable vapor pressure, and unlike ammonium nitrate, another known HME oxidizer, it is not known to readily dissociate producing vaporous products under normal ambient conditions (Ewing et al., "The vapor pressure of explosives" *Trends in Analytical Chemistry*, 42 (2013); Hosseini et al., "Thermal decomposition of pyrotechnic mixtures containing sucrose with either potassium chlorate or perchlorate" *Combustion and Flame*, 141, 322-326 (2005)). Nevertheless, it has been shown that trained canines can reliably find potassium chlorate alone and in mixtures with fuels (Lazarowski et al., "Explosives detection by military working dogs: Olfactory generalization from components to mixtures" *Applied Animal Behaviour Science,* 151, 84-93 (2014)) suggesting the presence of some associated volatile compounds composing the odor. It is generally assumed that canines detect such low volatility compounds via associated volatile compounds, known as the vapor signature, that are attributable to manufacture byproducts or decomposition of the materials. This is known to occur with other low volatility compounds, such as with explosives like RDX (1,3,5-Trinitro-1,3,5-triazinane), or with narcotics like cocaine, both of which exude characteristic vapor signatures that canines are able to detect as a proxy for the target material (Furton et al., "The scientific foundation and efficacy of the use of canines as chemical detectors for explosives" *Talanta,* 54, 487-500 (2001); Furton et al., "Identification of odor signature chemicals in cocaine using solid-phase microextraction-gas chromatography and detector-dog response to isolated compounds spiked on U.S. paper currency" *Journal of Chromatographic Science,* 40, 147-15 (2002)).

Chlorine has been detected in the headspace of potassium chlorate with the use of selected ion flow tube-mass spectroscopy (SIFT-MS) (Stevens et al., "Headspace analysis of inorganic materials" in *Trace Explosives Detection Workshop,* Ottawa, ON, Canada (2018)). Chlorine, however, is not amenable to either solid phase microextraction (SPME) or gas chromatography/mass spectrometry (GC/MS), though these techniques are generally the primary tools in the characterization of vapor signatures.

Gas chromatography with mass spectrometry (GC/MS) is a superior technique for separation with high sensitivity detection and analyte confirmation. Solvent-free pre-concentration can be added by pairing GC/MS with solid phase microextraction (SPME). SPME is a fast and portable headspace sampling technique in which a polymer-coated fiber is exposed to the headspace components of a given sample. Analytes ad- or absorb to the fiber coating and are then thermally desorbed directly in the heated inlet of a GC/MS. However, chlorine, being a small molecule with a very high vapor pressure, is not retained by commercially available GC separation columns or SPME fibers.

BRIEF SUMMARY

Disclosed herein is a method comprising: providing a fiber having propylene oxide adsorbed thereon; exposing the fiber to a gaseous sample; allowing the propylene oxide to react with any chlorine in the sample to form chloro-2-propanol.

BRIEF DESCRIPTION OF THE DRAWINGS

A more complete appreciation will be readily obtained by reference to the following Description of the Example Embodiments and the accompanying drawings.

DETAILED DESCRIPTION OF EXAMPLE EMBODIMENTS

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Chlorine is not well retained by the columns available for gas chromatography (GC) and for this reason, conventional GC-based detection methods are generally impractical for its identification at trace levels. Disclosed herein is a GC analysis method for trace chlorine to overcome this limitation. Central to this method, vaporous chlorine within a sample of gas to be analyzed is reacted with a derivatizing reagent, propylene oxide (also in the gas phase) to produce a GC-amenable derivative compound, chloro-2-propanol.

The disclosed reaction is based on the derivatization of ethylene oxide (EtO) by hydrobromic acid (HBr). Ethylene oxide has a wide range of industrial applications, but also is considered to be acutely toxic, leading OSHA to designate a health standard of 1 ppm as the maximum exposure limit. Previous methods of EtO detection included collection onto charcoal tubes followed by desorption and analysis by GC with flame ionization detection (FID), though this technique had a number of inadequacies (Esposito et al., "Determination of ethylene oxide in air by gas chromatography" *Analytical Chemistry,* 56, 1950-1953 (1984)). A method for the detection of EtO by GC using sampling tubes containing charcoal coated with hydrobromic acid (HBr) was first published in 1984 (Esposito) and was validated by OSHA in 1985 (Occupational Health and Safety Administration, "Ethylene Oxide, Method 50" Department of Labor, Salt Lake City, Utah (1985)). In this method EtO reacts with the HBr coating to produce 2-bromoethanol. This product was then extracted with dimethylformamide, further derivatized with heptafluorobutyrylimidazole, and finally analyzed by GC with electron capture detection (ECD). To date this method has continued to be the OSHA-recommended EtO detection method.

Instead of actively sampling of air containing ethylene oxide, in 2003 a method was published utilizing the same derivatization reaction of HBr with ethylene oxide by SPME, a static sampling technique, with analysis by GC with mass spectrometry (GC/MS) (Tsai et al., "Determination of ethylene oxide by solid-phase microextraction device with on-fiber derivatization" *Journal of Chromatography A*, 991, 1-11, (2003)). The method utilized a technique called sequential, on-fiber derivatization where the SPME fiber was first exposed to the derivatizing agent, HBr, then exposed the analyte of interest, in this case ethylene oxide. The derivatization product, 2-bromoethanol, was then formed on the fiber and analyzed by GC/MS.

Figure 1:
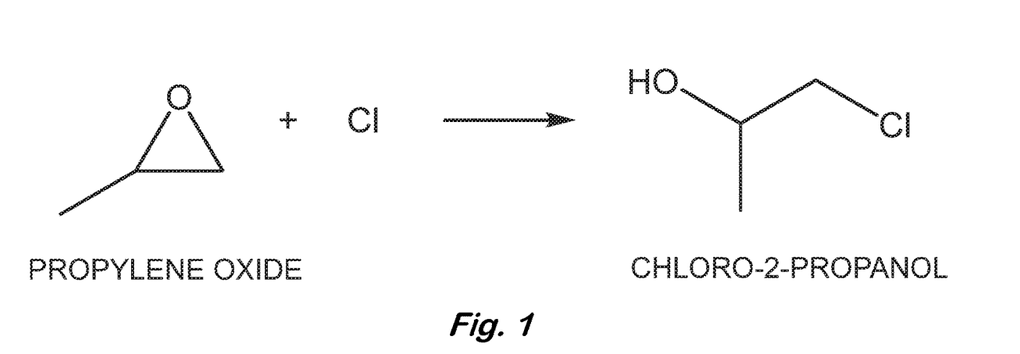
FIG. 1 shows the derivatization of chlorine by propylene oxide yielding chloro-2-propanol.

The method disclosed herein implements a similar reaction in reverse. Ethylene oxide is highly toxic, as mentioned above, and for this reason, propylene oxide—which is a more stable reagent—was used instead. However, ethylene oxide may also be used instead of propylene oxide. The resulting reaction, given in FIG. 1, uses propylene oxide as the derivatizing agent for gaseous chlorine, yielding chloro-2-propanol (C2P). This product is easily extracted and detected by SPME-GC/MS. Using this method, the headspace of potassium chlorate and related salts were interrogated for the presence of chloride, from vaporous HCl or $Cl_2$ with ambient water, in addition to other volatile species comprising the vapor signature of potassium chlorate. The method disclosed herein is not limited to any particular reaction mechanism, such as the one shown in FIG. 1. The form of the gaseous chlorine (e.g. ion, radical, molecule) has not been determined. It is believed that the hydrogen atom added to the product is derived from ambient water vapor.

Sequential, on-fiber derivatization SPME is performed for the detection of chlorine by GC/MS. For this purpose, neat propylene oxide is placed in a closed vial with septa and allowed to come to equilibrium. The vial septa is then pierced by the SPME plunger and the fiber (polydimethylsiloxane/divinyl benzene/carboxen coating sourced from Restek Inc. was used) is exposed to the vial headspace for a pre-determined extraction time. The fiber is then removed and immediately exposed to a vaporous chlorine source for another given extraction time. The fiber, now containing the derivatized product, is then inserted into the GC inlet for thermal desorption and analysis. The derivatization product, chloro-2-propanol, can be detected by GC/MS.

The method uses a fiber, such as, for example, a polydimethylsiloxane/divinylbenzene/carboxen solid phase microextraction fiber. The fiber includes adsorbed propylene oxide. As propylene oxide is a volatile liquid, one method of adsorbing it onto the fiber is to place the fiber in the headspace of a vessel containing propylene oxide.

The fiber is then exposed to a gaseous sample. The sample may simply be ambient air. It may also be a gas that has been collected from a source. For example, the fiber may be place near or in a container with a material suspected to contain potassium chlorate or another chlorine source. If the material does contain potassium chlorate, than the fiber may be exposed to its volatile products, including a form of chlorine.

The chlorine reacts with the propylene oxide to form chloro-2-propanol on the fiber. The fiber may then be injected into a gas chromatograph for detection of any chloro-2-propanol. The fiber may be warmed in the injector to desorb the chloro-2-propanol. It should be noted that the injection into the GC may be performed at any stage in the process. For example, with an appropriately configured injector such as that disclosed in US Pat. Appl. Pub. No. 2018/0246070, the propylene oxide may be absorbed onto the fiber and the fiber exposed to the sample all within the injector. It is also noted that the method disclosed and claimed herein may be performed in the absence of any detectable chlorine or potassium chlorate.

Potassium chlorate is not expected to decompose in temperatures under 356° C. (Hosseini et al., "Thermal decomposition of pyrotechnic mixtures containing sucrose with either potassium chlorate or perchlorate" *Combustion and Flame*, 141, 322-326 (2005)), and to this date no headspace components have been confirmed that could be utilized for vapor detection. However, the derivatization method described here was shown to enable characterization of halogen content in the headspace of potassium chlorate and other salts by SPME-GC/MS. With the use of on-fiber derivatization, chlorine as well as bromine was detected at different levels in the headspace of several variants of potassium chlorate, but not related chlorinated salts nor negative controls. Additionally, chlorine was detected in potassium chlorate—based explosive mixtures at the same time as other, underivatizated volatile species associated with the fuels.

The use of GC/MS for the detection of chlorine provides increased sensitivity and specificity over currently available methods. Addition of SPME, or another pre-concentration technique further improves method limit of detection for trace vapor samples. SPME is easily portable so sampling can be done in the field. The previously described derivatization method allows for chlorine gas to be extracted and detected by GC/MS.

This derivatization method is amenable to alternative sampling techniques. For example, this reaction could be used in the same way as the above-mentioned method of ethylene oxide vapor detection in which a sorbent material was impregnated with hydrobromic acid derivatizing agent allowing for the derivatization reaction to occur on the sorbent material (Esposito). Alternatively, another method for pre-concentration and derivatization of trace vapors using a cooled programmable temperature vaporizing (PTV) inlet with analysis by GC/MS has been described (US Pat. Appl. Pub. No. 2018/0246070). This type of "online" derivatization method could also be applicable to the previously described chlorine derivatization reaction.

The following examples are given to illustrate specific applications. These specific examples are not intended to limit the scope of the disclosure in this application.

Materials—The headspaces of potassium chlorate salts as well as related chlorine salts were analyzed. "Laboratory-grade" potassium chlorate, potassium chloride, potassium perchlorate, and sodium chlorate were purchased from Sigma-Aldrich (St. Louis, Mo.) and were at least 99% pure. Additional "industrial-grade" potassium chlorate was purchased from a pyrotechnic chemical supply company (Skylighter; Morro Bay, Calif.) containing 0.2% anti-caking agent (undefined). "Clandestine" potassium chlorate was harvested from matchstick heads (Diamond Greenlight Strike-on-the-Box Matches) using a clandestine methods described elsewhere (Defense Intelligence Agency, Homemade Explosives, 3rd Ed., Washington, D.C. (2014)). The derivatizing agent, propylene oxide (≥99.5%), and the internal standard, 1-octanol (≥99%), were both purchased from Sigma-Aldrich.

The headspaces of potassium chlorate explosive mixtures were also analyzed. These included the industrial-grade potassium chlorate mixed with petroleum jelly or vegetable oil (purchased from local supermarket).

Explosive handling—WARNING! Potassium chlorate mixed with a fuel source can be an explosive hazard. Proper handling, storage, and disposal precautions should be taken. Mixtures were prepared in static dissipative vials using wooden spatulas for stirring. The vials were then placed in a headspace-sampling chamber developed by the U.S. Naval Research Laboratory for explosives testing (DeGreeff et al., "Technical note: Headspace analysis of explosive compounds using a novel sampling chamber" *Forensic Science International*, 248, 55-60 (2015)), and allowed to equilibrate for 24 hours prior to extraction. All preparation and testing took place behind Explosive Personnel Shields (certified to a net explosives weight of 10.0 g). All extraction and analysis procedures were the same as that used for the other samples, and will be discussed below.

Headspace Extraction—The presence of chlorine in the headspace of potassium chlorate was investigated using on-fiber SPME derivatization by propylene oxide to produce chloro-2-propanol. To prepare the samples, 4.0 g of potassium chlorate (laboratory-grade, industrial-grade, clandestine, or related salt) was placed into individual 20 mL headspace vials with septa (Headspace Screw-Tread Vials, 18 mm; Restek; Bellefonte, Pa.). All samples were allowed to equilibrate in the closed vials for a minimum of 24 hours under ambient conditions. Samples were prepared in replicates of five including blank vials. Additionally, 2.0 mL of the derivatizing agent, propylene oxide, and the internal standard, 1-octanol, were deposited into separate vials, and were allowed to equilibrate for a minimum of 1 hr.

Headspace extraction was carried out using PDMS/DVB/CAR SPME fibers (Restek). Fibers were first inserted into the headspace of the propylene oxide vials for 15 seconds. They were then removed and reinserted into the headspace of the sample vials (or the headspace sampling chamber for the explosive materials) for a given amount of time. Extraction times ranging from 30 min to 17 hours were tested. Finally the fibers were inserted into the headspace of the internal standard for 5 seconds.

Instrument Analysis—For analysis, fibers were thermally desorbed in the inlet of a gas chromatograph (GC; Agilent 6890; Agilent Technologies; Santa Clara, Calif.) for 4 min at 260° C. Propylene oxide was discovered to remain absorbed to the SPME fibers even after 4 minutes of thermal desorption. As such, following desorption of the analytes, the fibers were inserted into 1.5 mL of methanol for 30 seconds and baked for three minutes in the GC inlet at 260° C. This process was repeated twice for each fiber to ensure complete removal of residual propylene oxide.

Separation occurred on an "Rtx-Volatile Amine" capillary column (30 m, 0.32 mm I.D., Restek; Bellefonte, Pa.) at a flow rate of 2 mL/min and a split ratio of 10:1. Oven temperature started at 35° C. (held for 0.50 min) and increased to 240° C. (held for 3.0 min) at 40° C./min. Analytes were detected by an Agilent 5975 mass selective detector (MS; Agilent Technologies). The MS source was maintained at 230° C. and the scan range was (m/z 30-300).

Figure 2:
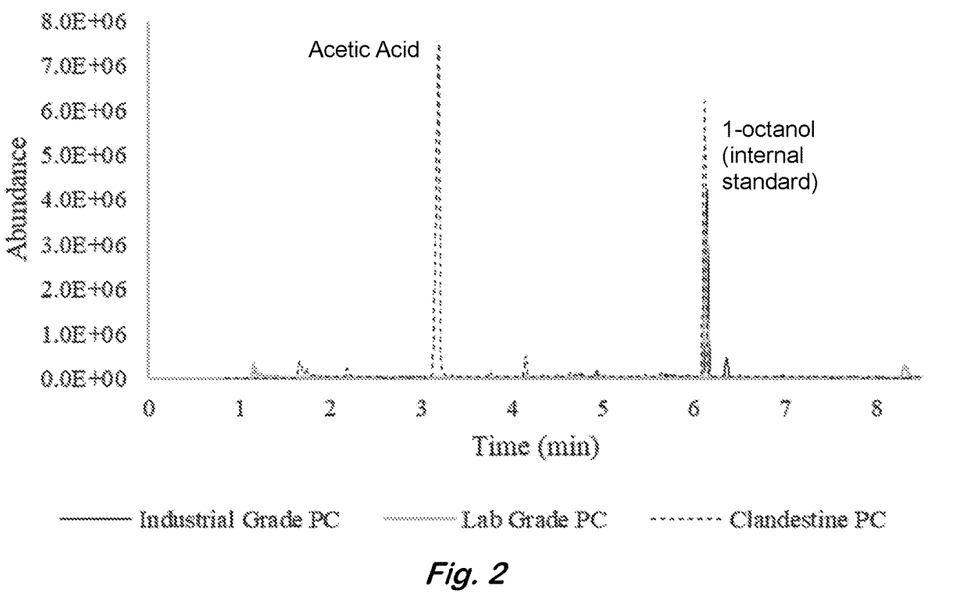
FIG. 2 shows reproduced chromatograms representing the headspace of three potassium chlorate (PC) variants, industrial-grade, laboratory-grade, and clandestine, without derivatizing agent.

Results and Discussion—Headspace analysis of the three potassium chlorate variants, laboratory-, industrial-, and clandestine-grades, were compared prior to addition of derivatizing agent in FIG. 2. The only major contributor to the headspace of any sample was acetic acid found solely in the clandestine sample. Low levels of additional volatile species were detected and are listed in Table 1.

TABLE 1

Headspace components detected above three potassium chlorate variants, industrial-grade, laboratory-grade, and clandestine, without derivatizing agents

| Headspace component: | Lab Grade | Industrial Grade | Clandestine |
|---|---|---|---|
| Methoxy-2-propanol acetate | | x | |
| Nonanal | | x | x |
| Carbon disulfide | x | | |
| Acetic Acid | | | x |
| Methoxy-phenyl-oxime | | | x |
| Acetamine | | | x |
| Triethylamine | | | x |
| Hexanal | | | x |

Figure 3:
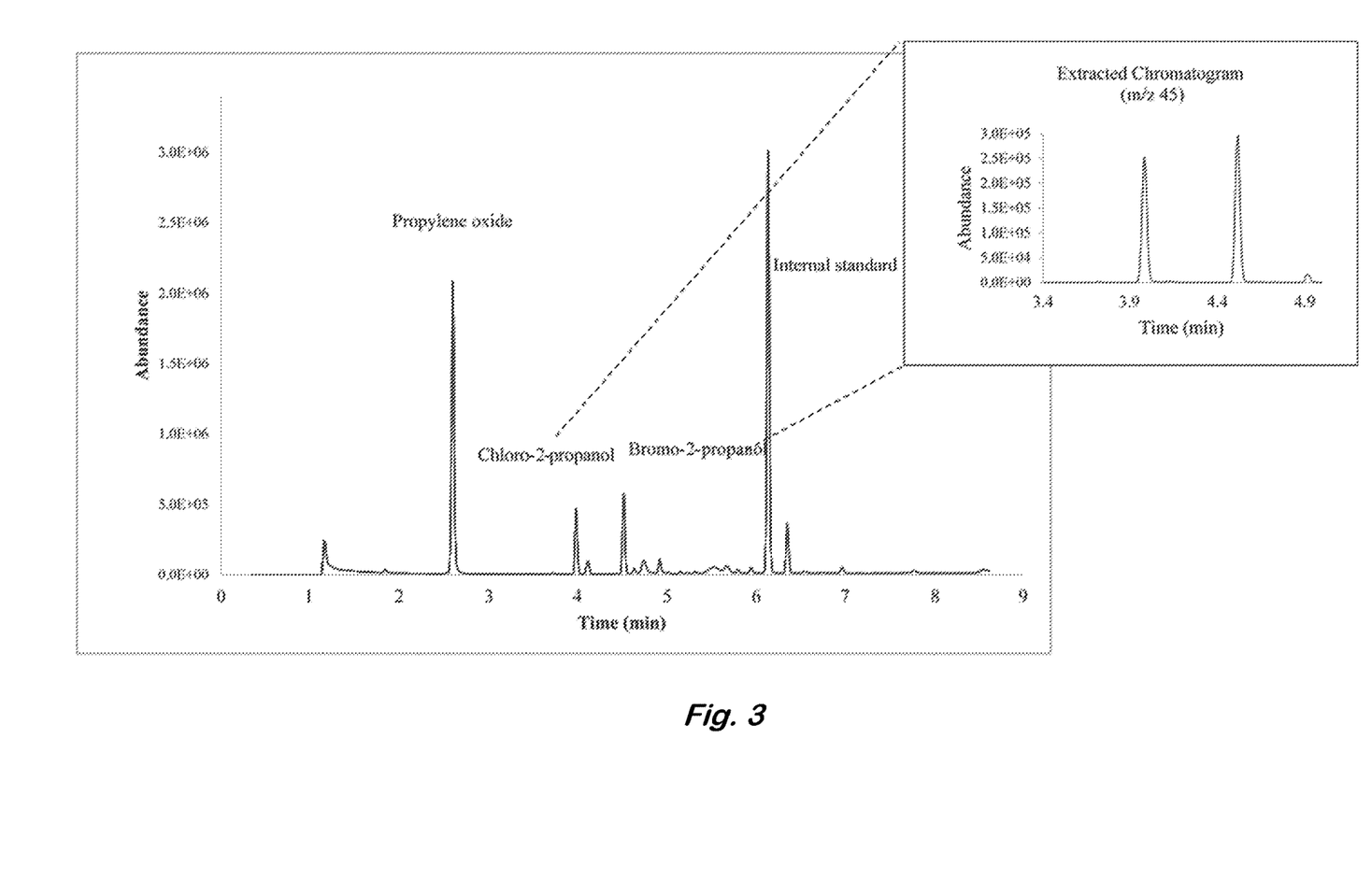
FIG. 3 shows a total ion chromatogram of industrial-grade potassium chlorate headspace with propylene oxide derivatizing agent. Inset chromatogram shows the extracted ion, m/z 45, indicating the presence of derivatized chlorine and bromine in the sample headspace.

Preliminary analyses were conducted with the industrial-grade potassium chlorate using the sequential on-fiber derivatization method, demonstrating the successful derivatization of chlorine product in the sample (FIG. 3). In addition to chlorine, the sample was discovered to contain unanticipated amounts of bromine, detected as bromo-2-propanol. Chloro-2-propanol eluted at a retention time of 3.9 min and bromo-2-propanol eluted at 4.5 min.

Figure 4:
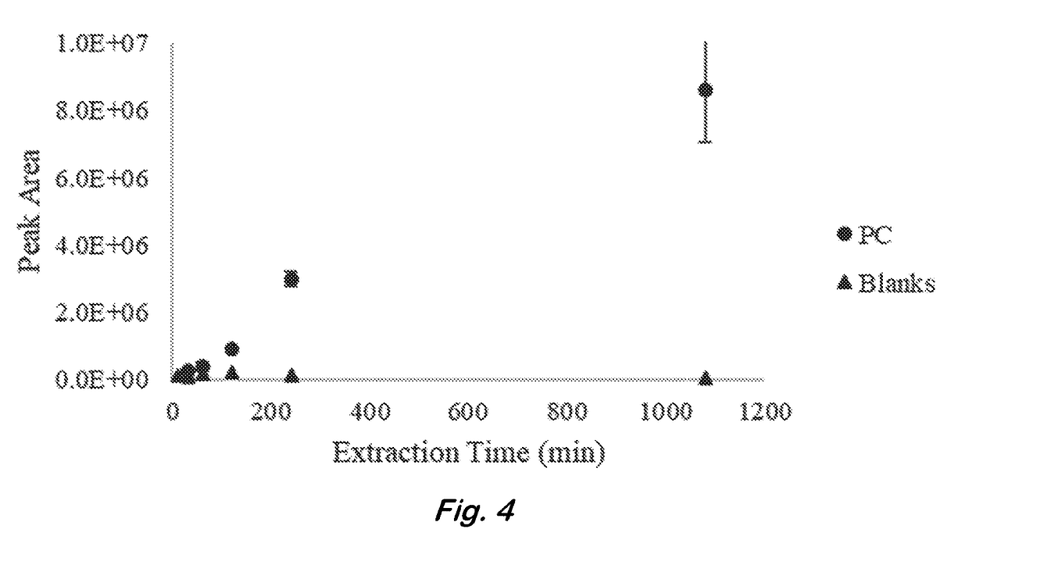
FIG. 4 shows the amount of derivatized chlorine (chloro-2-propanol) measured above industrial-grade potassium chlorate (PC) using varying SPME extraction times. Note. Error bars equal one standard deviation of the average value of at least three replicates.

Peak area was examined as a function of fiber extraction time to determine optimal extraction time (FIG. 4). A small quantity of chloro-2-propanol was detected above the blanks, but this was significantly lower than that detected above the potassium chlorate samples. It did not appear that equilibrium was reached even after an overnight extraction. For this reason, the maximum extraction time of 17 hours was chosen for future analyses. The slow SPME equilibration time could be due to the low level of chlorine present or the rate of the mechanism producing the chlorine, or a combination of both.

Figure 5:
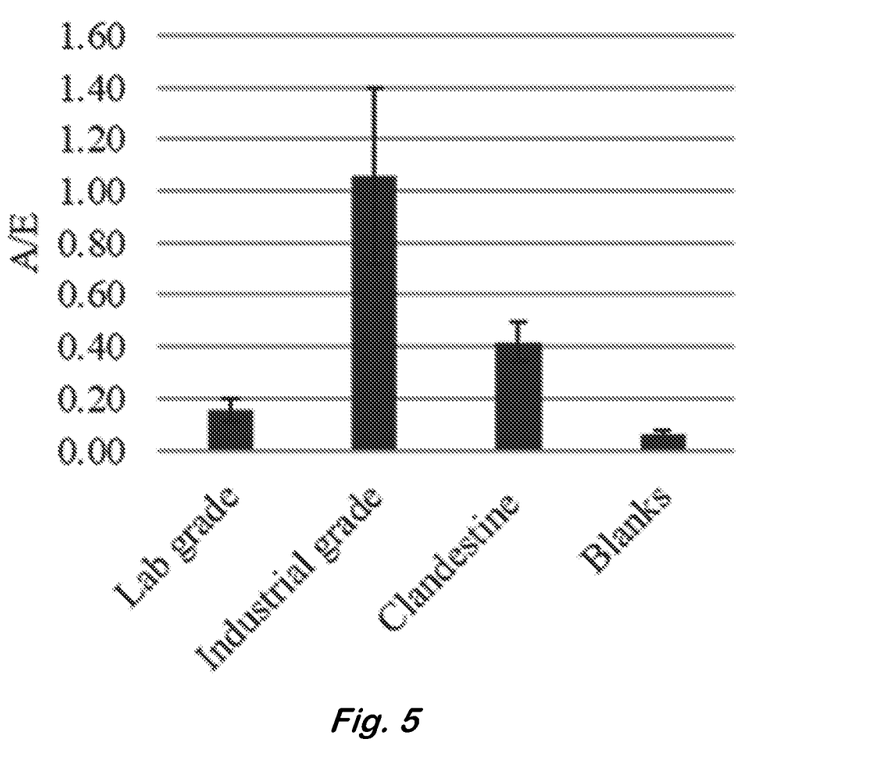
FIG. 5 shows relative amount of chlorine detected in the form of the derivatized product chloro-2-propanol from potassium chlorate samples. The relative abundance of chlorine in the headspace is measured as the chloro-2-propanol peak area divided by the peak area of the externally sampled internal standard (A/E).
Figure 6:
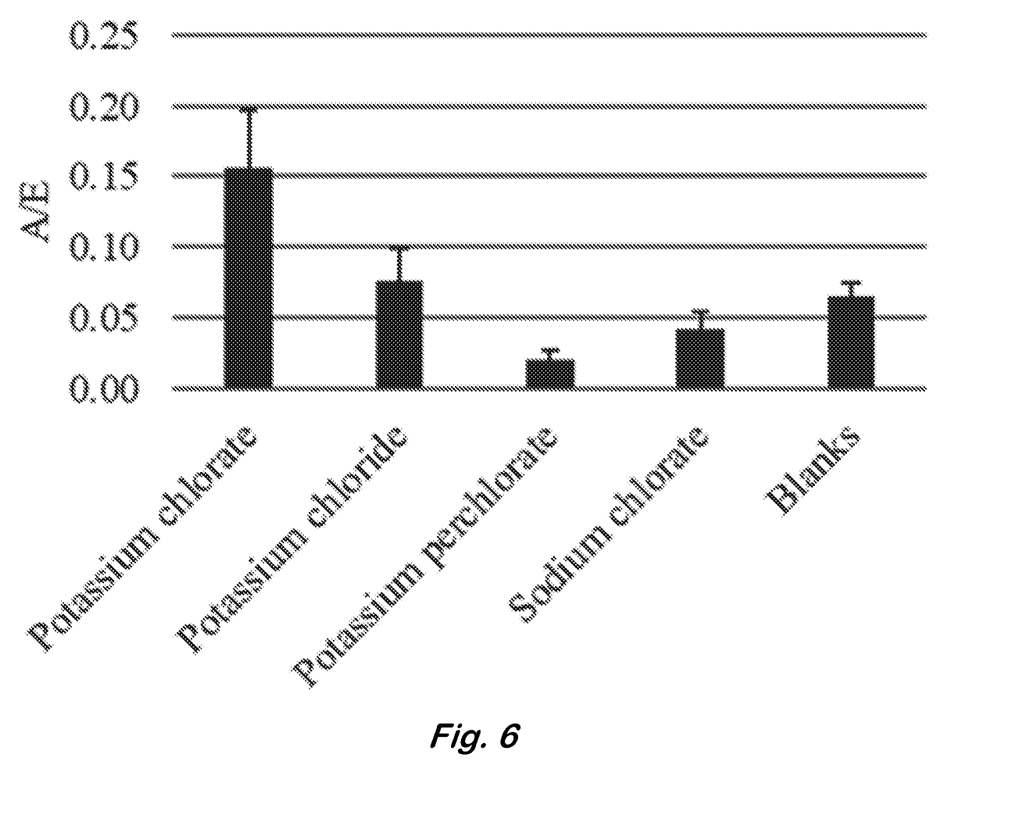
FIG. 6 shows relative amount of chlorine detected in the form of the derivatized product chloro-2-propanol from related laboratory-grade chlorinated salts. The relative abundance of chlorine in the headspace is measured as the chloro-2-propanol peak area divided by the peak area of the externally sampled internal standard (A/E).

The amount of chlorine in each potassium chlorate variant, as well as related chlorine salts, was compared using a ratio of the chloro-2-propanol peak area over the peak area of 1-octanol, the internal standard (FIG. 5). All potassium chlorate samples had significantly more chlorine than the blank vials (one-tailed t-test, 99+% confidence). The industrial grade was found to contain the most amount of chlorine in its headspace, followed by clandestine, and then laboratory-grade. The differences in quantity of chlorine measured from the three sources was likely due to differing purities and surface area, with the laboratory-grade being the most pure and the clandestine having the lowest surface area (due to imperfect grinding of the material). Interestingly, when measuring the chlorine above other chlorinated-salt samples (FIG. 6), only the potassium chlorate was significantly greater than the blank.

Figure 7:
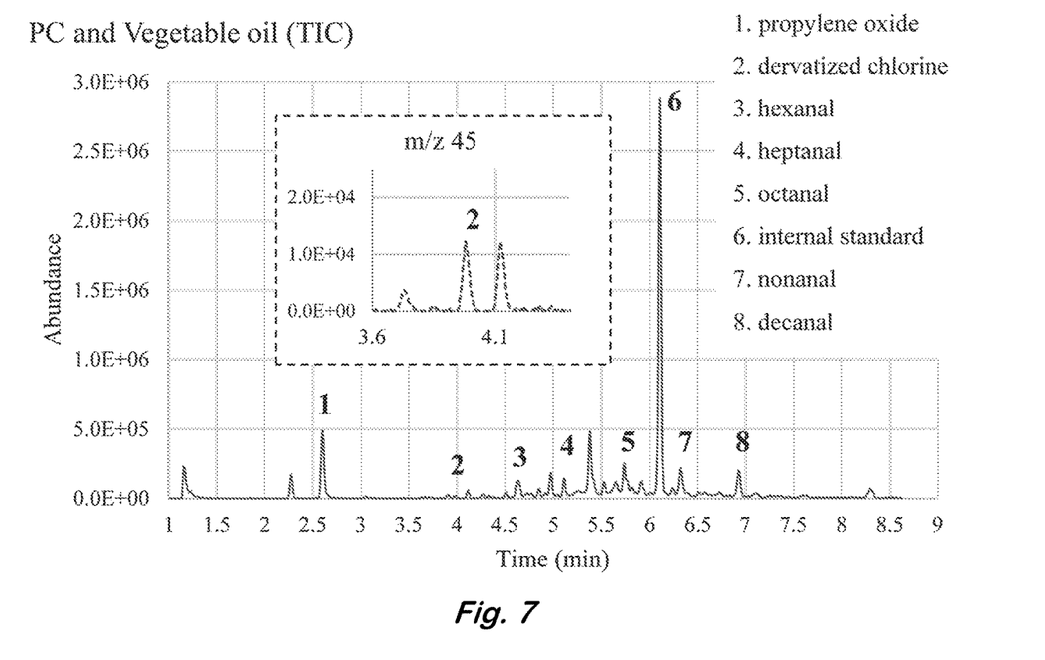
FIG. 7 shows a total ion chromatogram of the headspace above industrial-grade potassium chlorate/fuel explosive mixtures. Inset chromatogram shows the extracted ion, m/z 45, indicating the presence of derivatized chlorine and bromine in the sample headspace. Other volatile species related to the vegetable oil fuel are indicated by number.
Figure 8:
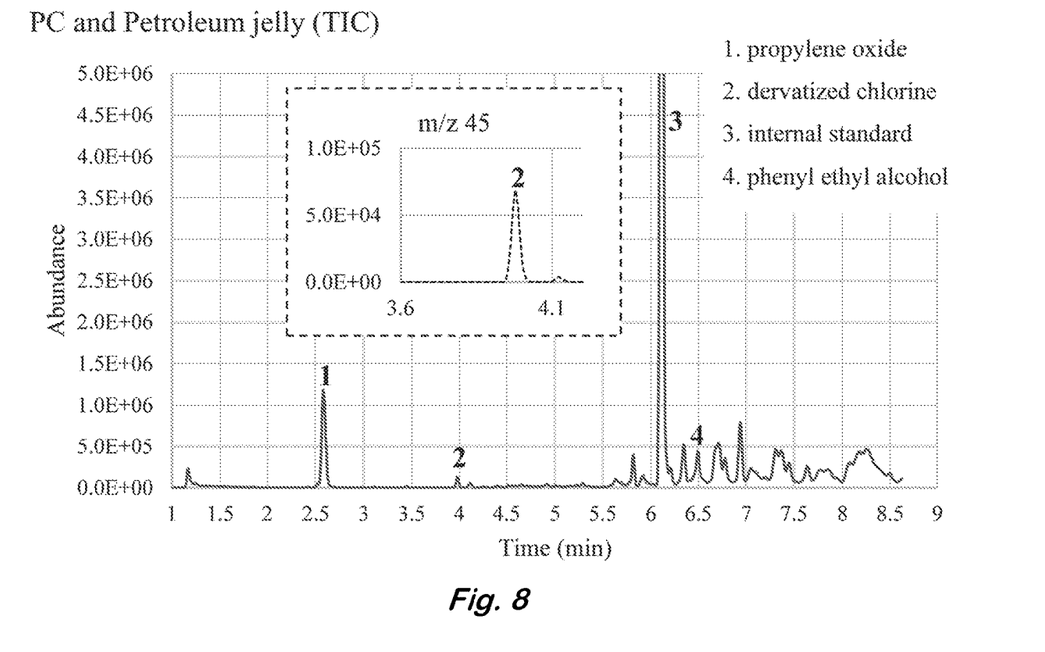
FIG. 8 shows a total ion chromatogram of the headspace above industrial-grade potassium chlorate/fuel explosive mixtures. Inset chromatogram shows the extracted ion, m/z 45, indicating the presence of derivatized chlorine and bromine in the sample headspace. Other volatile species related to the petroleum jelly fuel are indicated by number.

Finally, FIGS. 7-8 give chromatograms of the headspace above two potassium chlorate-based explosives. FIG. 7 depicts potassium chlorate mixed with vegetable oil. The derivatized chlorine, chloro-2-propanol, can be identified at approximately 3.9 min (see m/z 45 extracted ion trace), in addition to many volatiles associated with the vegetable oil. The C6-C10 aldehyde series associated with the vegetable oil (Jelen et al., "Headspace solid-phase microextraction use for the characterization of volatile compounds in vegetable oils of different sensory quality" *Journal of Agricultural and Food Chemistry*, 48(6), 2360-2367 (2000)) and labelled in the figure can be detected with no inference from the derivatizing agent. Likewise, FIG. 8 includes the chromatogram of the headspace from potassium chlorate mixed with petroleum jelly. Again, chloro-2-propanol is detected at approximately 3.9 min (as shown in the m/z 45 extracted ion trace) in addition to phenyl ethyl alcohol, the main volatile associated with the odor of petroleum jelly.

Obviously, many modifications and variations are possible in light of the above teachings. It is therefore to be understood that the claimed subject matter may be practiced otherwise than as specifically described. Any reference to claim elements in the singular, e.g., using the articles "a", "an", "the", or "said" is not construed as limiting the element to the singular.

What is claimed is:

1. A method comprising:
   providing a fiber having propylene oxide adsorbed thereon;
   exposing the fiber to a gaseous sample;
   allowing the propylene oxide to react with any chlorine and water vapor in the sample to form chloro-2-propanol.

2. The method of claim 1, wherein the fiber is a polydimethylsiloxane/divinylbenzene/carboxen solid phase microextraction fiber.

3. The method of claim 1, wherein providing the fiber comprises:
   placing the fiber in the headspace of a vessel containing propylene oxide; and
   allowing the propylene oxide to adsorb to the fiber.

4. The method of claim 1, wherein the gaseous sample is suspected of containing volatile products of potassium chlorate.

5. The method of claim 1, further comprising;
   injecting the fiber into a gas chromatograph; and
   detecting any chloro-2-propanol by gas chromatography.

6. A method comprising:
   providing a fiber having ethylene oxide adsorbed thereon;
   exposing the fiber to a gaseous sample;
   allowing the ethylene oxide to react with any chlorine and water vapor in the sample to form chloro-2-ethanol.

7. The method of claim 6, wherein the fiber is a polydimethylsiloxane/divinylbenzene/carboxen solid phase microextraction fiber.

8. The method of claim 6, wherein providing the fiber comprises:
   placing the fiber in the headspace of a vessel containing ethylene oxide; and
   allowing the ethylene oxide to adsorb to the fiber.

9. The method of claim 6, wherein the gaseous sample is suspected of containing volatile products of potassium chlorate.

10. The method of claim 6, further comprising;
    injecting the fiber into a gas chromatograph; and
    detecting any chloro-2-ethanol by gas chromatography.

11. The method of claim 1, wherein the gaseous sample is suspected of containing ionic, radical, or molecular chlorine.

12. The method of claim 6, wherein the gaseous sample is suspected of containing ionic, radical, or molecular chlorine.

* * * * *